(12) United States Patent
Kim

(10) Patent No.: US 8,070,697 B2
(45) Date of Patent: Dec. 6, 2011

(54) EXERCISE APPARATUS FOR BACKBONE REMEDY

(76) Inventor: Hag Chung Kim, Siheung-Si (KR)

( * ) Notice: Subject to any disclaimer, the term of this patent is extended or adjusted under 35 U.S.C. 154(b) by 816 days.

(21) Appl. No.: 12/160,774

(22) PCT Filed: Dec. 22, 2006

(86) PCT No.: PCT/KR2006/005651
§ 371 (c)(1),
(2), (4) Date: Jul. 11, 2008

(87) PCT Pub. No.: WO2007/075005
PCT Pub. Date: Jul. 5, 2007

(65) Prior Publication Data
US 2008/0312691 A1 Dec. 18, 2008

(30) Foreign Application Priority Data
Dec. 26, 2005 (KR) .................. 10-2005-0129259
Apr. 21, 2006 (KR) .................. 10-2006-0036230

(51) Int. Cl.
*A61F 5/00* (2006.01)
(52) U.S. Cl. ............... 601/24; 601/15; 601/26; 606/245
(58) Field of Classification Search ............ 601/5, 15, 601/23, 24, 26, 84, 89, 90, 91, 93, 97, 98, 601/101; 606/241–245; 602/32, 33; 5/613, 5/616, 618, 619, 621, 624, 648; 128/845
See application file for complete search history.

(56) References Cited

U.S. PATENT DOCUMENTS

| 4,245,626 | A | 1/1981 | Paolino | |
|---|---|---|---|---|
| 5,423,861 | A | 6/1995 | Kelley | |
| 6,277,141 | B1 * | 8/2001 | Lake | 606/243 |
| 7,189,214 | B1 * | 3/2007 | Saunders | 606/243 |
| 2004/0171974 | A1 | 9/2004 | Emsky | |

FOREIGN PATENT DOCUMENTS

| KR | 1019960010744 | 8/1996 |
|---|---|---|
| KR | 1020040082234 | 9/2004 |

* cited by examiner

*Primary Examiner* — Quang D Thanh
(74) *Attorney, Agent, or Firm* — Park & Associates IP Law, P.C.

(57) ABSTRACT

Disclosed herein is an exercise apparatus for backbone care, in which an exerciser's lower body is moved leftwards and rightwards when a lower body exercising panel rotates leftwards and rightwards, so that his or her upper body is moved in a direction opposite the moving direction of the lower body, and thus a slipped disk is restored to its original position and a bent section of the backbone is straightened. A sliding or slippery or a rotation mechanism is provided on an upper body exercising panel so that an exerciser's upper body is exercised naturally by the movement of the lower body. Thus, free rotation of the upper body exercising panel is possible even though additional power is not transmitted to the upper body exercising panel. The exercise apparatus allows exercise to be stably conducted in the shape of an S.

14 Claims, 3 Drawing Sheets

[Fig. 1]
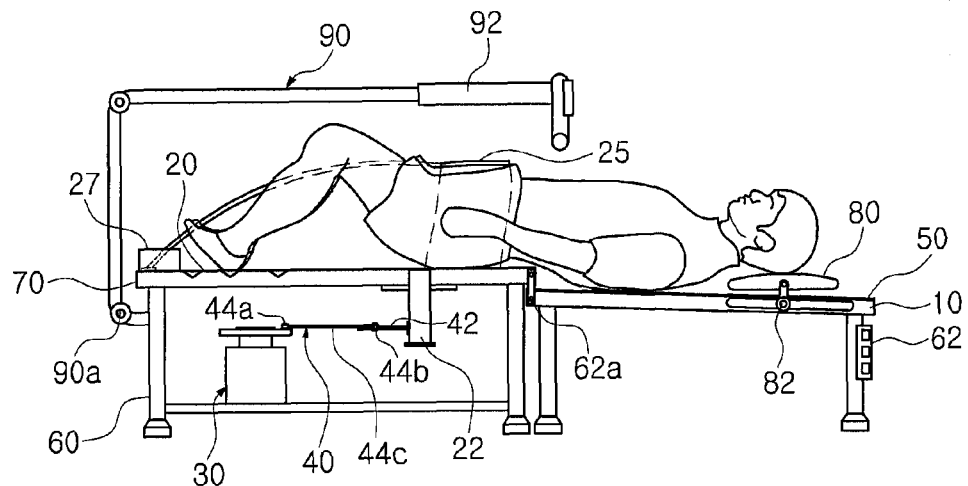
[Fig. 2]
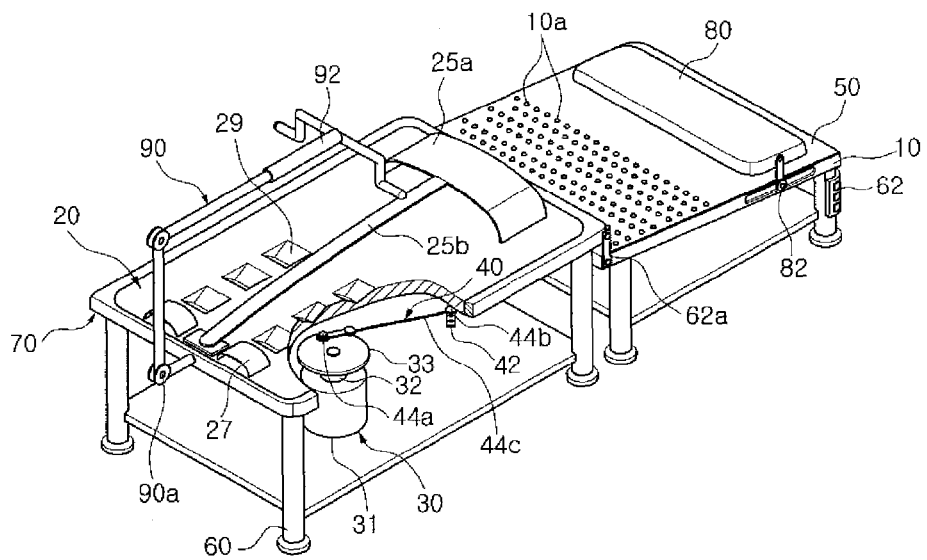
[Fig. 3]
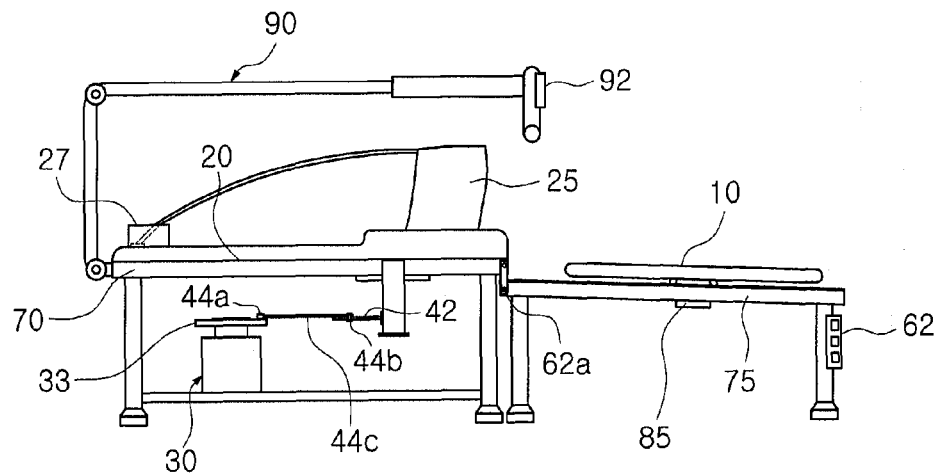

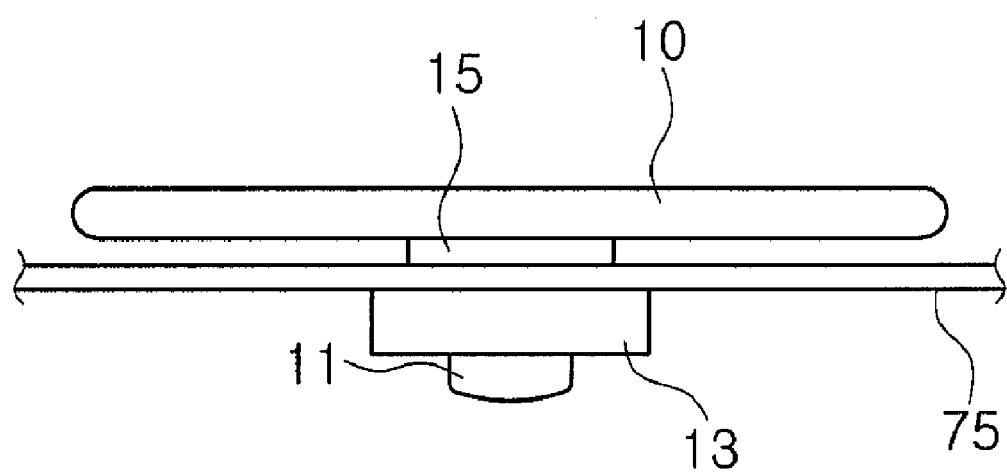
[Fig. 4]
[85: 15, 11, 13]

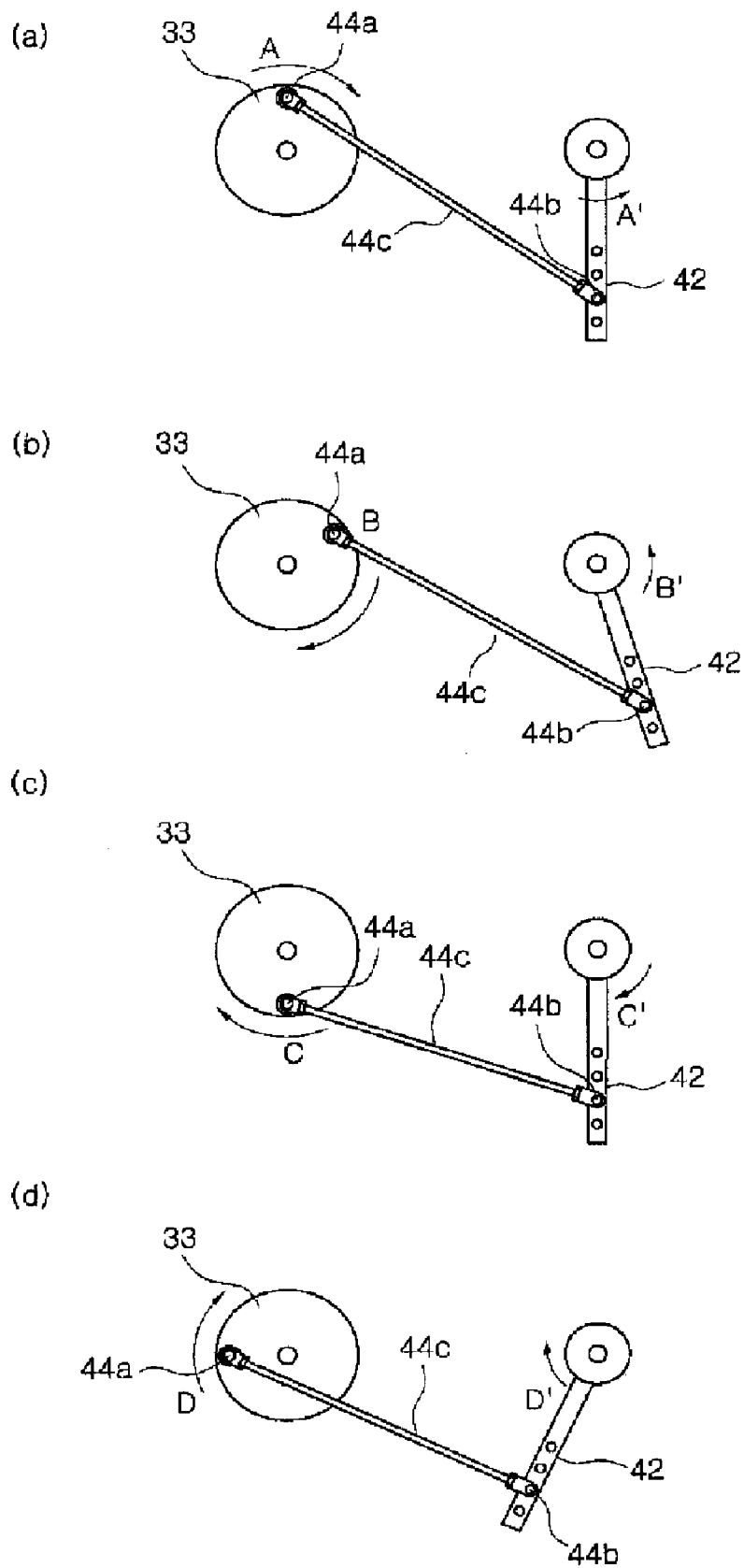
[Fig. 5]

EXERCISE APPARATUS FOR BACKBONE REMEDY

TECHNICAL FIELD

The present invention relates to an exercise apparatus for backbone care, which is constructed so that an upper body exercising panel and a lower body exercising panel are separated from each other, thus allowing the backbone to exercise smoothly in the shape of an S in a transverse direction.

More particularly, the present invention relates to an exercise apparatus for backbone care, in which an exerciser's lower body is moved leftwards and rightwards when a lower body exercising panel rotates leftwards and rightwards, so that his or her upper body is moved in the direction opposite the moving direction of the lower body, and thus a slipped disk is restored to its original position and the bent section of the backbone is straightened. The exercise apparatus of the invention is constructed so that an additional sliding means is provided on the upper body exercising panel or the upper body exercising panel freely rotates even if additional power is not transmitted to the upper body exercising panel. Such a construction allows the upper body to be naturally exercised by the exercise of the lower body, so that the flanks move in the direction opposite the moving direction of the buttocks when the buttocks move leftwards and rightwards. That is, the exercise apparatus allows exercise to be stably conducted in the shape of an S.

BACKGROUND ART

The backbone forms the center of a human's body, and is the body part through which all nerves, transmitting instructions from the brain, pass. Thus, it is obvious that the health of the backbone is representative of the health of the entire body.

As the body ages, exercise is not conducted for a long time, or a person acquires a bad habit or poor posture in daily life, the backbone slowly bends leftwards, rightwards or forwards, so that overall health is worsened, and resistance to many diseases is lowered. In this case, a person may suffer from a ruptured disk, which is caused by abnormal protrusion of a spinal disk and causes pain due to pressure on spinal nerves, or scoliosis, which is the lateral deformation of the vertebral column.

As a method of treating the ruptured disk or scoliosis, a so-called "goldfish exercise" is known to people. The goldfish exercise is recommended especially for a person whose backbone is bent to the left or right. The goldfish exercise is conducted by bending the body leftwards or rightwards as if a person were a swimming goldfish, after he or she lies on his or her back. This exercise corrects the dislocation of the left and right sections of the backbone, eliminates pressure on spinal nerves or paralysis of peripheral nerves, makes the nervous function of the whole body uniform, and permits the smooth circulation of blood.

A conventional exercise apparatus using the above goldfish exercise has been proposed. Korean Patent Laid-Open Publication No. 10-2004-82234, which is entitled "Waist Strengthening Apparatus" and was published on Sep. 24, 2004, includes a straightening unit which shakes only an exerciser's buttocks leftwards and rightwards, in the state in which he or she is lying on his or her back. However, the straightening unit is problematic in that it shakes only the buttocks leftwards and rightwards in the state in which an exerciser is lying on his or her back, so that the shaking of the upper body is insufficient. That is, the main point of the goldfish exercise is to shake the upper body leftwards and rightwards. However, the conventional exercise apparatus exercises only the buttocks, so that there is little movement of the upper body.

DISCLOSURE OF INVENTION

Technical Problem

Accordingly, the present invention has been made keeping in mind the above problems occurring in the prior art, and an object of the present invention is to provide an exercise apparatus, in which an additional sliding means is provided on an upper body exercising panel, thus allowing the pelvis to be sufficiently moved leftwards and rightwards as a lower body exercising panel rotates, and allowing the upper body to be exercised in conjunction with the leftward and rightwards movement of the lower body.

Another object of the present invention is to provide an exercise apparatus, in which a rotation means, which is freely rotatable even though additional power is not transmitted to an upper body exercising panel, is provided on the upper body exercising panel, so that the upper body is naturally exercised by the exercise of the lower body, thus allowing natural and stable letter-"S" exercise to be conducted.

A further object of the present invention is to provide an exercise apparatus, in which an upper body exercising panel is constructed such that the upper body is inclined downwards, thus allowing exercise to be conducted from the pelvis to the head in the shape of an S when a lower body exercising panel moves, with the backbone pulled upwards due to the weight of the head and the shoulder.

Yet another object of the present invention is to provide an exercise apparatus, which allows exercise to be conducted in the state in which an exerciser does not stretch his or her legs, but bends the legs, and in which the heels are secured to pre-determined positions such that the toes point upwards, thus allowing a large quantity of motion to be realized in a short period of time.

Technical Solution

In order to accomplish the above objects, the present invention provides an exercise apparatus for backbone care, including an upper body exercising panel, a lower body exercising panel which is arranged to be higher than the upper body exercising panel and performs reciprocating motion relative to a rotating shaft coupled to the bottom of the lower body exercising panel, a drive means for moving the lower body exercising panel, a link means coupling the rotating shaft of the lower body exercising panel with the drive means, a sliding means provided on the upper body exercising panel, and support legs for supporting the upper body exercising panel and the lower body exercising panel.

Further, a rotation means is provided on the bottom of the upper body exercising panel, thus naturally rotating an exerciser's upper body by motion of the lower body exercising panel without using additional power.

Advantageous Effects

As described above, the present invention provides an exercise apparatus, which is constructed so that an exerciser's upper body is exercised naturally by the exercise of his or her lower body even though additional power is not transmitted to an upper body exercising panel, and thus his or her buttocks are moved leftwards or rightwards and simultaneously his or her flanks are bent rightwards or leftwards in the direction opposite the moving direction of the buttocks, therefore providing a stable motion in the shape of an "S".

According to the present invention, the upper body is laid on a far infrared radiation plate, which is smooth and is heated by a heating element. Thus, in the state in which the muscles and the ligaments in the region of the back are softened, the buttocks and the legs are directly exercised. Hence, the body part from the pelvis to the head is moved naturally in the shape of an S, so that the spinal column and the cervical vertebrae are smoothly exercised. As a result, scoliosis, that is, the lateral curve of the backbone, is corrected, and nerves and muscles distributed around the backbone become comfortable. Further, when the waist is moved leftwards and rightwards, the internal organs are also shaken, so that gas is eliminated from the bowels, and thus constipation is cured.

Further, when the upper body is inclined downwards, the backbone is pulled by to the weight of the head and the shoulders, so that the gaps between the vertebrae are increased. In such a state, when the upper body is shaken leftwards or rightwards, the slipped disk is restored to its original position, so that an effective remedy is achieved.

BRIEF DESCRIPTION OF THE DRAWINGS

FIG. 1 is a side view showing the use of an exercise apparatus for backbone care, according to the present invention;

FIG. 2 is a perspective view showing the use of the exercise apparatus for backbone care, according to the present invention;

FIG. 3 is a side view showing an exercise apparatus for backbone care, according to another embodiment of the present invention;

FIG. 4 is an enlarged side view showing an upper body exercising panel included in the exercise apparatus of FIG. 3; and FIGS. 5a to 5d are views showing the operating stages of a drive means of the exercise apparatus, according to the present invention.

DESCRIPTION OF REFERENCE CHARACTERS OF IMPORTANT PARTS

10: upper body exercising panel
20: lower body exercising panel
30: drive means 40: link means
50: sliding means 60: support legs
70: frame 75: frame of upper body exercising panel
80: head supporting member
85: rotation means 25: fastening belt
27: ankle belt 29: heel supporting depressions

BEST MODE FOR CARRYING OUT THE INVENTION

Hereinafter, the preferred embodiments of the present invention will be described in detail with reference to the accompanying drawings.

As shown in FIGS. 1 and 2, a lower body exercising panel 20 is coupled to a frame 70 which is supported by support legs. A drive motor 31 is installed under the lower body exercising panel such that a drive rotating shaft 32 faces upwards. A rotary disc 33 is attached to the drive rotating shaft 32, with a hole bored in the rotary disc 33 so that a first rod end 44a is inserted into the hole. A first rod end 44a is fastened using a bolt and a nut such that the first rod end is placed on the rotary disc 33.

A connection plate 42 is welded to an area on the outer circumferential surface of a rotating shaft 22 of the lower body exercising panel. A second rod end 44b is attached to the end of the connection plate, and is coupled to the first rod end 44a via a rod 44c. That is, the first and second rod ends 44a and 44b and the rod 44c, which couple the rotary disc 33 with the lower body exercising panel 20, constitute a link means 40.

Here, a rotating shaft support plate (not shown) is attached to the lower surface of the lower body exercising panel 20, and a hole corresponding to the inner diameter of a bearing (not shown) is bored through the support plate. Afterwards, the bearing is secured to the upper surface of the support plate using a housing. In this case, since the inner circumference of the bearing is in close contact with the outer circumference of the rotating shaft, the bearing functions to support the lower body exercising panel so that the lower body exercising panel does not shake up and down, in addition to allowing the lower body exercising panel to be smoothly rotated leftwards and rightwards.

Generally, the lower body exercising panel 20 has the shape of a plane. However, in order to enhance the exercise effect, it is preferable that a step be formed on the lower body exercising panel 20 at a position adjacent to an upper body supporting part. That is, although not shown in the drawings, if the portion of the lower body exercising panel that supports the buttocks is higher due to the step, an exerciser's body is inclined gradually downwards from the buttocks to the head or the toes, like a bow, when he or she lies on the exercise apparatus. Such a construction increases the contact area of the exerciser's back with the lower body exercising panel and the upper body exercising panel, thus maximizing the exercise effect.

Preferably, the step of the lower body exercising panel 20 is 3 cm to 6 cm higher than the surface of the lower body exercising panel 20. The edge of the step is rounded to prevent an exerciser's waist from being scratched or injured.

Next, the construction of the upper body exercising panel 10 will be described below. A sliding means 50 is provided on the upper surface of the upper body exercising panel. As described above, the upper body can be naturally exercised merely by exercising the lower body, without providing an additional exercising means to the upper body exercising panel. Thus, the sliding means 50 may be provided on the upper portion of the upper body exercising panel 10 using a slippery material. For more efficient sliding motion, cloth, such as cotton flannel, or a slippery plate, which is the same size as an exerciser's back, may be placed on the upper body exercising panel. Further, rollers may be attached to the upper body exercising panel in the longitudinal direction thereof, thus allowing the upper body to naturally slide leftwards and rightwards. In this case, the slipperiness of the slippery material used for the sliding means 50 is sufficient as long as the upper body is rotated in the direction opposite the lower body while the waist is bent, when the lower body is rotated leftwards and rightwards by the drive means. It is difficult to represent the slipperiness as a numerical value.

Further, an insulating material is provided on the upper body exercising panel, and a heating element is provided on the insulating material. Thereafter, a far infrared radiation plate for radiating far infrared rays, such as germanium, is installed. Especially, the sliding means, which is provided on the upper surface of the upper body exercising panel, may be embodied by the far infrared radiation plate, which radiates far infrared rays, such as germanium. Further, the heating element is provided on the upper body exercising panel, so that an exerciser can move his or her body leftwards and rightwards without the body becoming stiff or the backbone moving excessively.

The upper body exercising panel may be constructed as shown in FIG. 3. That is, an additional frame 75 is provided to support the upper body exercising panel. The upper body exercising panel 10 may be coupled to the upper portion of the frame via an additional rotation means 85. That is, the upper body exercising panel 10 is not rotated by external power. As the lower body exercising panel 20 is rotated leftwards and rightwards, an exerciser's lower body, especially the buttocks and the waist, move leftwards and rightwards. Due to the movement of the lower body, the upper body is naturally moved rightwards and leftwards. The upper body exercising panel of the invention is characterized in that the upper body exercising panel is coupled to the rotation means 85, which is not operated by power, so that the upper body exercising panel is naturally rotated by the movement of an exerciser's upper body.

In a detailed description, as shown in FIGS. 3 and 4, a rotary rod 11 is coupled to the lower surface of the upper body exercising panel 10, and a bearing is fitted over the rotary rod. That is, in order to support the load acting on the rotary rod 11 and the weight of the rotary rod, the bearing is preferably mounted to the outer circumferential surface of the rotary rod. Any kind of bearing may be mounted to the rotary rod. However, a thrust bearing is generally used. Further, a through part, which has a size corresponding to the cross-section of the rotary rod 11, is formed in the frame 75 to which the upper body exercising panel 10 is coupled, and the rotary rod coupled to the upper body exercising panel 10 is inserted into the through part. That is, a rotary rod support plate 13 extends downwards from the frame 75 by about 5 cm. A pre-determined portion of the support plate 13 is bored by the inner diameter of the bearing, and the bearing is secured to the support plate 13 via a housing. Next, the rotary rod 11 passes through the bearing to be inserted therein, and the upper body exercising panel 10 is provided on the rotary rod 11. In this case, when an exerciser lies on the upper body exercising panel 10, the upper body exercising panel 10 contacts the bearing, so that smooth rotation is impossible. In order to solve this problem, a step 15 is preferably formed on the top of the rotary rod. Thus, the rotary rod 11, the bearing, and the support plate 13 constitute the rotation means 85.

The construction of the lower body exercising panel will be described below. In order to prevent an exerciser's upper body from being pulled upwards when the lower body exercising panel is rotated, a belt 25 is attached to the lower body exercising panel. As shown in FIGS. 1 and 2, the belt may preferably comprise a transverse belt 25a that surrounds an exerciser's belly and buttocks. Moreover, it is more preferable to also provide a longitudinal belt 25b. One end of the longitudinal belt is coupled to a predetermined portion of the transverse belt 25a, while the other end of the longitudinal belt is coupled to the center of the lower portion of the lower body exercising panel. The longitudinal belt 25b prevents an exerciser's upper body from being pulled upwards when he or she exercises, thus preventing the buttocks from being dislodged from the lower body exercising panel 20. That is, the longitudinal belt is additionally provided, thus allowing an exerciser to exercise more stably. More preferably, the transverse belt 25a comprises a Velcro fastener so as to effectively secure the lower body.

Moreover, guide members (not shown) may also be provided on both sides of the frame 70 of the lower body exercising panel so as to prevent an exerciser's lower body from being dislodged from the lower body exercising panel when the lower body exercising panel is rotated leftwards and rightwards. Of course, guide members (not shown) may also be provided on the upper body exercising panel 10.

An exerciser may exercise with his or her legs extended. However, as shown in FIG. 1, he or she may exercise with his or her knees bent. To this end, a support means is required to support the feet on the lower body exercising panel 20. As the support means, heel supporting depressions 29 are provided in the lower body exercising panel, so that an exerciser's heels are inserted into the heel supporting depressions and thereby his or her feet are supported. Particularly, in the present invention, the reason why an exerciser exercises with his or her knees bent is because there is a significant difference between the quantity of motion when the legs are not extended but the knees are drawn up and the quantity of motion when the legs are extended. According to this invention, since an exerciser exercises with his or her legs not extended, the lower body exercising panel can be shortened, so that the exercise apparatus itself can have a compact structure. Thus, the exercise apparatus can be installed in a small space in a home, thus affording convenient use.

Further, the heel supporting depressions 29 prevent the entire soles of the feet from contacting the lower body exercising panel, but cause the heels to be inserted into the heel supporting depressions such that the toes point toward the ceiling. Such a construction increases the quantity of motion. Preferably, several heel supporting depressions are arranged on the lower body exercising panel, thus allowing the heels to be supported according to the length of an exerciser's leg.

Conversely, when an exerciser exercises with his or her legs extended, the lower body is preferably secured using ankle belts 27.

As shown in FIGS. 1 and 2, a handle 90 is installed to allow an exerciser to easily lie and sit up while sitting on the lower body exercising panel. A control box is provided on the middle portion of the handle so as to control the power and speed of a motor and the temperature of a heater, thus allowing an exerciser to control the starting or stopping operation of exercise and control the speed himself or herself while lying on the exercise apparatus. A length adjusting means 92 may be provided on the handle 90 to adjust the length or height according to the size of an exerciser's body. Further, a hinge 90a is provided at a bent portion of the handle 90, thus allowing the height to be easily adjusted.

Turning back to the construction of the upper body exercising panel 10, the upper body exercising panel is preferably positioned to be lower than the lower body exercising panel 20, in consideration of the quantity of motion. In order to adjust the height of the upper body exercising panel 10, the upper body exercising panel is preferably coupled to the frame 70 using a hinge 62a. Further, the height difference between the upper body exercising panel 10 and the lower body exercising panel 20 is preferably set at about 3 cm. Such a height difference maximizes the quantity of motion, in addition to allowing an exerciser to comfortably lie on the exercise apparatus. As such, the upper body exercising panel is oriented at an incline, so that an exerciser's upper body tends to move out of the rotating line due to centrifugal force during a rotating motion. Thereby, the interval between the vertebrae is increased, so that a backbone straightening effect is naturally realized.

Of course, an inclination adjusting means 62 is preferably provided to adjust the inclination of the upper body exercising body 10 according to an exerciser's features and the quantity of motion. The inclination adjusting means 62 is operated along with the hinge 62a, thus adjusting the height and inclination of the upper body exercising panel.

Further, an additional height adjusting means may be provided to adjust the height between the upper body exercising panel and the lower body exercising panel, if necessary.

Further, as shown in FIG. 2, a plurality of protuberances 10a is formed on the upper surface of the upper body exercising panel 10, and provides an acupressure effect to the upper body when the upper body is moved leftwards and rightwards. Moreover, a head supporting member 80 is further provided on the upper body exercising panel. A rotating shaft (not shown) may be coupled to the head supporting member 80 so as to permit free rotation of the head supporting member. That is, when the upper body is moved leftwards and rightwards relative to the lower body exercising panel, the head is not moved leftwards and rightwards in a horizontal direction, but is moved along a circular path. Thus, in order to permit the free movement of the head, the rotating shaft (not shown) is preferably provided. Further, a distance adjusting means 82 may be provided on the head supporting member 80 to adjust the distance between the head supporting member and the lower body exercising panel. As shown in FIGS. 1 and 2, the distance adjusting means includes grooves which are formed on both sides of the upper body exercising panel 10 and have a predetermined length, rollers which are inserted into the grooves to move forwards and backwards, and coupling members which couple the rollers with the head supporting member.

The operation of the present invention, constructed as described above, will be described below with reference to the accompanying drawings.

First, an exerciser regulates the temperature of the upper body exercising panel 10, and then turns on a heater switch. In order to sufficiently rotate the pelvis, the buttocks and feet are placed on the lower body exercising panel 20 with the legs bent. At this time, the two feet are not together, but are placed on the lower body exercising panel such that the interval between the two feet is about 20 cm. Further, the transverse belt 25a is fastened to the pelvis region. If necessary, the longitudinal belt 25b is also fastened to the body.

Subsequently, the exerciser grasps the handle 90 and slowly lies down on the upper body exercising panel. After the position of the head supporting member is adjusted to be suitable for his or her head, the rotating speed of the motor is appropriately controlled using the control box according to the condition of his or her body. In such a state, the exercise apparatus is turned on, thus operating the lower body exercising panel.

As shown in FIGS. 5a to 5d, when the drive motor 31 is driven at a preset speed, the rotary disc 33 continues to rotate in one direction. It is preferable that the rotary disc rotate in a clockwise direction. When the first link end 44a coupled to the lower body exercising panel 20 reaches position A, the connection plate 42, which is connected to the rotating shaft 22 attached to the lower body exercising panel, is pulled by the rod 44c and reaches position A'. When the rotary disc 33 of the drive motor continues to rotate, so that the first link end 44a reaches position B, the rotating shaft of the lower body exercising panel is located at position B'. When the rotary disc 33 reaches position C, the rotating shaft of the lower body exercising panel moves to position C'. Subsequently, when the rotary disc 33 reaches position D, the rotating shaft of the lower body exercising panel is located at position D'. When the rotary disc of the drive motor continues to rotate and returns to its original position, the rotating shaft returns to its original position. The starting position of the first link end 44a is illustrated as one example. It is not necessary for the first link end 44a to start moving from position A. The first link end may start moving from any position. The important feature of the invention is that the first link end 44a is rotated by the rotation of the rotary disc 33, and that the connection plate 42 coupled to the first link end is moved leftwards and rightwards only, so that the lower portion of the lower body exercising panel is fixed and the upper portion of the lower body exercising panel is rotated leftwards and rightwards while drawing an imaginary fan shape.

At this time, the pelvic bone placed on the lower body exercising panel is moved leftwards and rightwards, and the backbone coupled to the pelvic bone is moved leftwards and rightwards. Further, the muscles and the ligaments of the upper body are softened by far infrared rays and heat, so that the upper body can be moved leftwards and rightwards without overstraining the backbone and the muscles.

Further, the horizontal rotating range of the lower body exercising panel may be adjusted by changing the length of the rod 44c. The final length of the rod 44c is determined according to whether the second rod end 44b of the rod 44c is coupled to any one of holes of the connection plate 42, and determines the rotating range of the lower body exercising panel.

Further, although not shown in the drawings, a plurality of holes may be formed in the rotary disc 33. The holes change the coupling position of the first rod end 44a, thus adjusting the length of the rod 44c.

The invention claimed is:

1. An exercise apparatus for backbone care, comprising:
   an upper body exercising panel;
   a lower body exercising panel arranged to be higher than the upper body exercising panel, for performing reciprocating motion relative to a rotating shaft coupled to a bottom of the lower body exercising panel;
   drive means for moving the lower body exercising panel; and
   link means coupling the rotating shaft of the lower body exercising panel with the drive means.

2. The exercise apparatus according to claim 1, further comprising:
   sliding means provided on the upper body exercising panel.

3. The exercise apparatus according to claim 1, wherein rotation means is provided on a bottom of the upper body exercising panel, thus naturally rotating an exerciser's upper body by motion of the lower body exercising panel without using additional power.

4. The exercise apparatus according to claim 1, wherein a step is formed at a position on the lower body exercising panel supporting an exerciser's buttocks, so that the exerciser's body is inclined downwards from the buttocks to the head when the exerciser lies on the exercise apparatus.

5. The exercise apparatus according to claim 1, further comprising:
   a head supporting member provided on the upper body exercising panel.

6. The exercise apparatus according to claim 5, wherein the head supporting member comprises a rotating shaft so as to permit free rotation of the head supporting member.

7. The exercise apparatus according to claim 5, further comprising:
   distance adjusting means provided on the head supporting member to adjust a distance according to a user's height.

8. The exercise apparatus according to claim 1, further comprising:
   a fastening belt provided on the lower body exercising panel and fastening an exerciser's lower body to the lower body exercising panel, wherein the fastening belt comprises:

a transverse belt surrounding the exerciser's belly and preventing the lower body from shaking; and a longitudinal belt coupled at a first end thereof to a predetermined portion of the transverse belt, and coupled at a second end thereof to a predetermined portion of the lower body exercising panel.

9. The exercise apparatus according to claim 1, further comprising:
a heel supporting depression provided at a predetermined position on the lower body exercising panel, so that an exerciser's heel is inserted into the heel supporting depression.

10. The exercise apparatus according to claim 1, further comprising:
inclination adjusting means provided on the upper body exercising panel, and adjusting an inclination of the upper body exercising panel relative to the lower body exercising panel.

11. The exercise apparatus according to claim 1, further comprising:
heating means provided on either of or both of the upper body exercising panel and the lower body exercising panel.

12. The exercise apparatus according to claim 11, wherein the heating means comprises an insulating plate, a heating element provided on the insulating plate, and a far infrared radiation plate provided on the heating element.

13. The exercise apparatus according to claim 1, wherein the drive means comprises:
a drive motor;
a drive rotating shaft rotated by the drive motor; and
a rotary disc rotated by rotation of the drive rotating shaft, and
the link means comprises:
a connection plate connected to an outer circumferential surface of the rotating shaft of the lower body exercising panel; and
a link member coupling the connection plate with the rotary disc, whereby the lower body exercising panel coupled to the link means is reciprocated by rotation of the rotary disc.

14. The exercise apparatus according to claim 13, wherein a rotating range of the lower body exercising panel is determined according to a coupling position of the link member with holes formed in the connection plate or the rotary disc.

* * * * *